US006168916B1

(12) United States Patent
Kingsman et al.

(10) Patent No.: US 6,168,916 B1
(45) Date of Patent: Jan. 2, 2001

(54) HOST ADAPTATION OF RETROVIRAL VECTORS

(75) Inventors: Alan John Kingsman; Susan Mary Kingsman, both of Oxon (GB); Paula Marie Cannon, South Pasadena, CA (US); Martin Andreas Nowak, Oxford (GB)

(73) Assignee: Oxford Biomedica (UK) Limited, Oxford (GB)

( * ) Notice: Under 35 U.S.C. 154(b), the term of this patent shall be extended for 0 days.

(21) Appl. No.: 09/091,305

(22) PCT Filed: Dec. 16, 1996

(86) PCT No.: PCT/GB96/03104

§ 371 Date: Oct. 21, 1998

§ 102(e) Date: Oct. 21, 1998

(87) PCT Pub. No.: WO97/22709

PCT Pub. Date: Jun. 26, 1997

(30) Foreign Application Priority Data

Dec. 15, 1995 (GB) .................................................. 9525639

(51) Int. Cl.[7] ........................... C12N 5/10; C12N 15/867; C12N 15/64; C12Q 1/70
(52) U.S. Cl. ................................... 435/5; 435/6; 435/7.1; 435/455; 435/456; 435/235.1; 435/236; 435/237; 435/325; 435/320.1
(58) Field of Search ............................ 435/5, 6, 7.1, 455, 435/456, 235.1, 236, 237, 325, 320.1

(56) References Cited

U.S. PATENT DOCUMENTS 4,211,843  7/1980  Dubreuil et al. .................. 424/212.1

FOREIGN PATENT DOCUMENTS

| WO 90/06770 | 6/1990 | (WO) . |
| WO 93/25698 | 12/1993 | (WO) . |
| WO 94/11524 | 5/1994 | (WO) . |
| WO 94/27643 | 12/1994 | (WO) . |
| WO 95/07358 | 3/1995 | (WO) . |

OTHER PUBLICATIONS

Maryse Etienne–Julan, Pierre Roux, Serge Carillo, Philippe Jeanteur and Marc Piechaczyk; "The efficiency of cell targeting by recombinant retroviruses depends on the nature of the receptor and the composition of the artificial cell–virus linker"; *Journal of Gneral Virology;* 1992; pp. 3251–3255.
Francois–Loic Cosset, Yasuhiro Takeuchi, Jean–Luc Battini, Robin A. Weiss, and Mary K. L. Collins; "High–Titer Packaging Cells Producing Recombinant Retroviruses Resistant to Human Serum"; *Journal of virology;* vol. 69, No. 12, pp. 7430–7436, Dec. 1995.
John H. Holland; "Genetic Algorithms"; *Scientific American;* Jul. 1992; pp. 44–50.

Richard A. Morgan, et al.; "Human Gene Therapy"; *Annu. Rev. Biochem;* 1993; pp. 191–217.
Jeanne R. McLachlin, et al.; "Retroviral–Mediated Gene Transfer"; *Progress in Nucleic Acid Research and Molecular biology;* 1990; vol. 38, pp. 91–135.
Stephen Goff, et al.; "Isolation and Properties of Moloney Murine Leukemia virus Mutants: Use of a Rapid Assay for Release of Virion Reverse Transcriptase"; *Journal of virology;* Apr. 1981; vol. 38, No. 1, pp. 239–248.
E. Hunter, et al.; "Retrovirus Envelope Glycoproteins"; *Current Topics in Microbiology and Immunology;* 1990; vol. 157, pp. 187–253.
Suraiya Rasheed, et al.; "Amphotropic Host Range of Naturally Occurring Wild Mouse Leukemia viruses"; *Journal of virology;* Jul. 1976; vol. 19, No. 1, pp. 13–18.
Janet W. Hartley, et al.; "Naturally Occurring Murine Leukemia Viruses in Wild Mice: Characterization of a New "Amphotropic" Class"; *Journal of virology;* vol. 19, No. 1, pp. 19–25, 1976.
Marja Van Zeijl, et al.; "A human amphotropic retrovirus receptor is a second member of the gibbon ape leukemia virus receptor family"; *Proc. Natl. Acad. Sci.;* Feb. 1994; vol. 91, pp. 1168–1172.
David E. Ott, et al.; "Phenotypes of Murine Leukemia Virus–Induced Tumors: Influence of 3' Viral Coding Sequences"; *Journal of virology;* Oct. 1992; vol. 66, No. 10, pp. 6107–6116.
Sandrine Valsesia–Wittmann, et al.; "Modifications in the Binding Domain of Avian Retrovirus Envelope Protein to Redirect the Host Range of Retroviral Vectors"; *Journal of Virology;* Jul. 1994; vol. 68, No. 7, pp. 4609–4619.
Yasuhiro Takeuchi, et al.; "Type C Retrovirus Inactivation by Human Complement Is Determined by both the Viral Genome and the Producer Cell"; *Journal of Virology;* Dec. 1994; vol. 68, No. 12, pp. 8001–8007.
Te–Hua Tearina Chu, et al.; "Retroviral Vector Particles Displaying the Antigen–Binding Site of an Antibody Enable Cell–Type–Specific Gene Transfer"; *Journal of Virology;* Apr. 1995; vol. 69, No. 4, pp. 2659–2663.
Jean–Luc Battini, et al.; "Receptor Choice Determinants in the Envelope Glycoproteins of Amphotropic, Xenotropic, and Polytropic Murine Leukemia viruses"; *Journal of virology;* Mar. 1992; vol. 66, No. 3, pp. 1468–1475.

(List continued on next page.)

*Primary Examiner*—David Guzo
(74) *Attorney, Agent, or Firm*—Merchant & Gould P.C.

(57) ABSTRACT

A method of making retrovirus vectors having selected characteristics, in particular an increased ability to infect a particular target cell, comprises subjecting a starting retrovirus or retroviral vector to a selection process in vitro which involves a plurality of rounds of infection of a host cell during which the retrovirus or retroviral vector evolves to attain the selected characteristics. Components of the evolved retrovirus or retroviral vector can be used in retroviral vector production systems for producing retroviral vectors having the selected characteristics. The invention is particularly useful for preparing retroviral vectors suitable for gene therapy.

20 Claims, 6 Drawing Sheets

OTHER PUBLICATIONS

Francois–Loic Cosset, et al.; "Retroviral Retargeting by Envelopes Expressing an N–Terminal Binding Domain"; *Journal of Virology;* Oct. 1995; vol. 68, No. 10, pp. 6314–6322.

Daniel G. Miller, et al.; "Cloning of the cellular receptor for amphotropic murine retroviruses reveals homology to that for gibbon ape leukemia virus"; *Proc. Natl. Acad. Sci.;* Jan. 1994; vol. 91, pp. 78–82.

Xiaoliang Han, et al.; "Ligand–directed retroviral targeting of human breat cancer cells"; *Proc. Natl. Acad. Sci.;* Oct. 1995; vol. 92, pp. 9747–9751.

Nikunj V. Somia, et al.; "Generation of targeted retroviral vectors by using single–chain variable fragment: An approach to in vivo gene delivery"; *Proc. Natl. Acad. Sci.;* Aug. 1995; vol. 92, pp. 7570–7574.

Jane C. Burns, et al.; "Vesicular stomatitis virus G glycoprotein pseudotyped retroviral vectors: Concentration to very high titer and efficient gene transfer into mammalian and nonmammalian cells"; *Proc. Natl. Acad. Sci.;* Sep. 1993; vol. 90, pp. 8033–8037.

Joshua R. Sanes, et al.; "Use of a recombinant retrovirus to study post–implantation cell lineage in mouse embryos"; *EMBO Journal;* 1986; vol. 5, No. 12, pp. 3133–3142.

Lorraine M. Albritton, et al.; "A Putative Murine Ecotropic Retrovirus Receptor Gene Encodes a Multiple Membrane–Spanning Protein and Confers Susceptibility to Virus infection"; *Cell;* May 19, 1989; vol. 57, pp. 659–666.

Noriyuki Kasahara, et al.; "Tissue–Specific Targeting of Retroviral Vectors Through Ligand–Receptor Interactions"; *Science;* Nov. 25, 1994; vol. 266, pp. 1373–1376.

Mariann Grossman, et al.; "Successful ex vivo gene therapy directed to liver in a patient with familial hypercholesterolaemia"; *Nature Genetics;* Apr. 1994; vol. 6, pp. 335–341.

Steven A. Rosenberg, et al.; "Gene Transfer into humans–immunotherapy of patients with advanced melanoma, using tumor–infiltrating lymphocytes modified by retroviral gene transduction"; *New England Journal of Medicine;* Aug. 30, 1990; pp. 570–578.

Yuko Soneoka, et al.; "A transient three–plasmid expression system for the production of high titer retroviral vectors"; *Nucleic Acids Research;* 1995; vol. 23, No. 4, pp. 628–633.

Roger D. Cone, et al.; "High–efficiency gene transfer into mammalian cells: Generation of helper–free recombinant retrovirus with broad mammalian host range"; *Proc. Natl. Acad. Sci.;* Oct. 1984; vol. 81, pp. 6349–6353.

Daniel T. Gillespie; 1976; *Journal of Computational Physics;* pp. 403–434; "A General Method for Numerically Simulating the Stochastic Time Evolution of Coupled Chemical Reactions".

S. Kirkpatrick, et al.; May 13, 1983; *Science;* vol. 220, pp. 671–680; "Optimization by Simulated Annealing".

Walter Fontana, et al.; Sep. 15, 1989; *Physical Review A;* vol. 40, No. 6, pp. 3301–3321; "Physical aspects of evolutionary optimization and adaptation".

Martin Nowak.; Oct. 11, 1990; *Nature;* vol. 347, pp. 522; "HIV mutation rate".

Vinay K. Pathak, et al.; May 1992; *Journal of virology;* vol. 66, No. 5, pp. 3093–3100; "5–Azacytidine and RNA Secondary Structure Increase the Retrovirus Mutation Rate".

A. Schober, et al.; 1995; *BioTechniques;* vol. 18, No. 4, pp. 652–661; "Multichannel PCR and Serial Transfer Machine as a Future Tool in Evolutionary Biotechnology".

Manfred Eigen, et al.; 1988; *J. Phys. Chem.;* pp. 6881–6891; "Molecular Quasi–Species".

A. Dusty Miller, et al.; 1989; *BioTechniques;* vol. 7, No. 9, pp. 980–990; "Improved Retroviral Vectors for Gene Transfer and Expression".

Fig. 3.
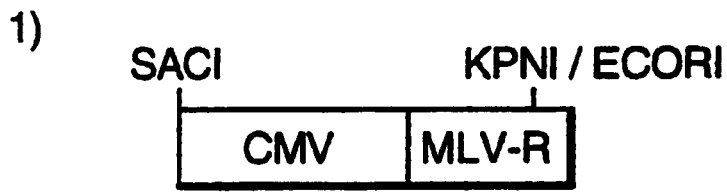
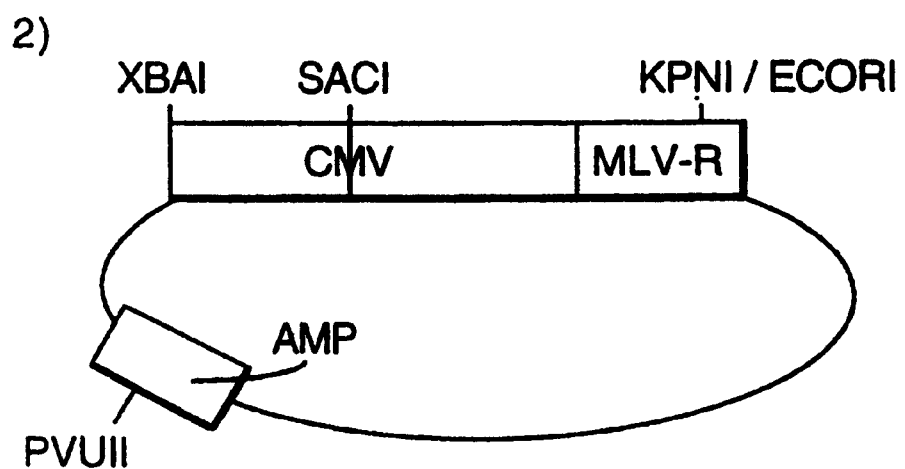
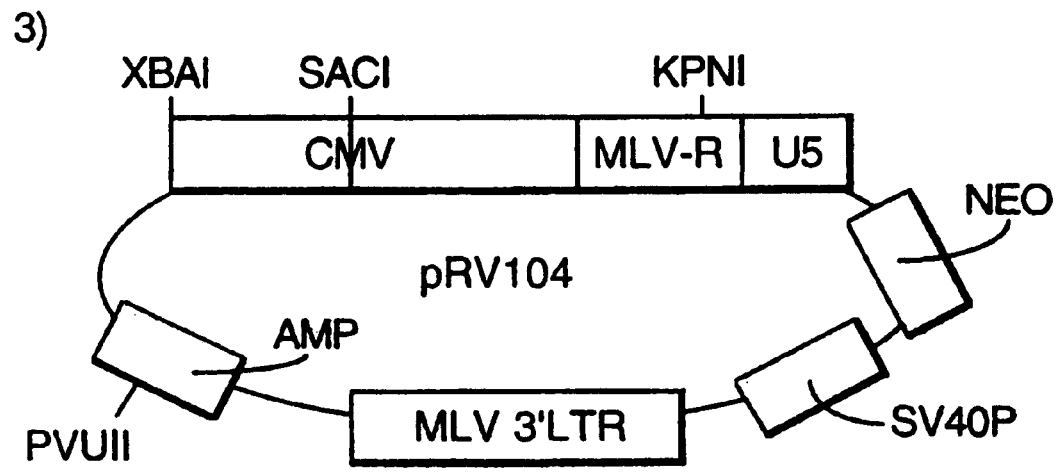

SEQUENCE LISTING

<160> NUMBER OF SEQ ID NOS: 4

<210> SEQ ID NO 1
<211> LENGTH: 39
<212> TYPE: DNA
<213> ORGANISM: Synthetic primer

<400> SEQUENCE: 1
cgcggatccg aattcatggg ccagactgtt accactccc                39

<210> SEQ ID NO 2
<211> LENGTH: 42
<212> TYPE: DNA
<213> ORGANISM: Synthetic primer

<400> SEQUENCE: 2
cgcgtcgact ctagattagg gggcctcgcg ggtttaacct ta            42

<210> SEQ ID NO 3
<211> LENGTH: 39
<212> TYPE: DNA
<213> ORGANISM: Synthetic primer

<400> SEQUENCE: 3
cgcgctagct ctagaatggc gcgttcaacg ctctcaaaa                39

<210> SEQ ID NO 4
<211> LENGTH: 34
<212> TYPE: DNA
<213> ORGANISM: Synthetic primer

<400> SEQUENCE: 4
cgcggatcct catggctcgt actctatggg tttt                     34

HOST ADAPTATION OF RETROVIRAL VECTORS

This invention relates to improvements in retroviral vectors for gene therapy and other uses. In particular the invention relates to methods for producing improved retroviral vectors, and for producing improved retroviruses which may be used to make retroviral vectors. The invention further relates to the retroviruses and retroviral vectors produced by such methods and to retroviral production systems and packaging cell lines derived using the retroviruses and retroviral vectors.

Within the field of gene therapy retroviral vectors are the most widely used gene delivery system. The most commonly used retroviral vectors are based on murine leukaemia virus (MLV). Furthermore, MLV-based vectors are the only retroviral vectors that have been used in human clinical trials (Morgan & Anderson 1993). MLV is a simple C-type retrovirus, the molecular biology of which has been reviewed extensively. The commonly used vectors are usually produced using packaging cells lines containing integrated copies of a gag-pol expression cassette and an env expression cassette (McClaughlin et al 1990). A plasmid encoding the vector genome (RNA) is transfected into the packaging cell to produce the RNA species that is packaged into the viral particles encoded by gag-pol and env. The retroviral particles so produced generally have one of two distinct tropisms. If the env gene in the packaging cell encodes envelope proteins from an ecotropic virus then the retroviral vector will transduce only murine and rat cells. If the env gene is from an amphotropic virus then the vector will transduce a broader range of cell types including human cells. The determinants of tropism reside substantially, therefore, in the envelope protein(s) (Hunter & Swanstrom, 1990). In particular the variable regions known as VRA and VRB determine whether the surface protein (SU, gp70) binds the ecotropic or amphotropic receptors (Baftini et al, 1992). The ecotropic receptor is the murine basic amino acid transporter (Albritton et al 1989) and the amphotropic receptor is a widely distributed phosphate transporter (Miller et al 1994; VanZeijl et al, 1994). In order to transduce human cells for therapeutic purposes amphotropic vectors are used.

Amphotropic vectors are derived from natural amphotropic MLV variants, isolated in 1976, that are capable of infecting a wide range of cell types (Rasheed et al., 1976; Hartley and Rowe, 1976). These vectors were first produced in the mid-1980s (e.g. Cone and Mulligan, 1984) using components from the original viruses. Although amphotropic vectors transduce human cells these vectors are generally an order of magnitude less efficient at transducing human cell lines compared with their efficiency on murine cells. Also, even though they are being used widely for gene therapy trials in man the efficiency of transduction is very variable from primary cell type to cell type (Rosenberg et al., 1990; Grossman et al., 1994) and this seriously limits the usefulness of these systems. The origin of this variability is not known.

There is a need for retroviral vectors which are more efficient at transducing human cells. There is also a need for retroviral vectors which are more suited than existing vectors for gene therapy in humans or other uses of retroviral vectors such as induction of disease mimics in animals. The invention addresses these needs.

The invention provides in one aspect a method of making a retroviral vector having one or more selected characteristics, which method comprises:
(i) providing a starting retrovirus or retroviral vector, and a host cell for the retrovirus or the retroviral vector;
(ii) subjecting the starting retrovirus or retroviral vector to a selection process in vitro which selection process involves a plurality of rounds of infection of the host cell during which the retrovirus or retroviral vector evolves to attain the selected characteristic or characteristics; and
(iii) where a starting retrovirus is provided in (i), using the retrovirus resulting from (ii) in at least one component of a retroviral vector production system for producing retroviral vectors having the selected characteristic or characteristics.

Thus, by a process which may generally be described as evolution in vitro, a retroviral vector can be produced which has characteristics more suited to a chosen purpose. A selected characteristic according to the invention will be associated with the genome of the retrovirus or retroviral vector resulting from the selection process (ii). The starting retrovirus or retrovirus vector will generally be a population of retrovirus or retrovirus vectors, which population evolves in vitro in the method according to the invention.

In another aspect, the invention provides retroviral vectors made by a method as described herein.

In a further aspect the invention provides a retroviral vector production system, said system having at least one component associated with a selected characteristic or characteristics attained by a method as described herein and transferred from the retrovirus or retroviral vector into the retroviral vector production system.

The retroviral vector production system preferably comprises a packaging cell line transfected with a DNA construct encoding a packagable retroviral vector genome. The selected characteristic or characteristics may be associated with the vector genome or with one or more components of the packaging cell line, or with both.

In still further aspects, the invention provides expression vectors comprising components of retroviral vector production systems, which components are derived from retroviruses or retroviral vectors resulting from a selection process as described herein. The invention also provides methods of making retroviral vector production systems which systems comprise such components.

The starting retrovirus or retroviral vector may be derived from any suitable retrovirus or retroviruses. MLV is presently the most extensively studied retrovirus in this field and MLV-based vectors have been used in gene therapy. The invention is not however limited to MLV-based vectors. Suitable retroviruses include other oncoretroviruses (the sub-group of retroviruses of which MLV is a member), or lentiviruses (which include HIV, SIV, FIV, BLV, EIAV, CEV and visna virus), or retroviruses from other sub-groups.

The term retroviral vector is used here to describe a defective retrovirus which is not by itself replication competent. However, it is capable of infection of a host cell, and thus has a genome which is capable of integrating into the host cell genome and has a packaging signal. Thus, a retroviral vector usually lacks at least one of the packaging components gag-pol, and env. When a starting retroviral vector is used in the method according to the invention, the host cell will need to contain the missing packaging component or components in order that infection of the host cell by the vector may result in the production of further retroviral vector particles.

A starting retrovirus contains functional env and gag-pol in its genome and is replication competent. Even so, a starting retrovirus is not necessarily a wild type retrovirus; generally it will have been modified in some way while still remaining replication competent. The use of modified retroviruses is preferred because these can be wellcharacterised and designed to meet certain needs. For example, for practical reasons it may be necessary to include a selectable marker in the genome of the starting virus, so that infected host cells can be selected for. Also, it may be preferable for the virus genome to be under the transcriptional control of a high efficiency promoter such as the cytomegalovirus (CMV) promoter, in place of the viral LTR U3 promoter. The purpose of this would be to ensure that viral genome production in infected cells is not a rate-limiting step during the selection process, so that a characteristic such as more efficient infection can be effectively selected for. These features of the genome may be employed in the genome of a starting retroviral vector as well as a starting retrovirus.

Selection conditions are imposed in the method of the invention according to the characteristic or characteristics it is desired to achieve. A preferred characteristic for selection according to the invention is an improved ability to infect a particular target cell type. However, the invention is not limited to characteristics relating to infection. Other desired characteristics may be selected for such as an improved ability to is withstand harsh conditions, either chemical or physical. Selection processes for characteristics such as these are also described in detail herein.

The basic steps of infection of a target cell by a retrovirus or retroviral vector include attachment to the target cell and entry into the cell via surface proteins in particular the envelope protein encoded by env, unpackaging of the RNA genome, reverse transcription of the genome to produce a double-stranded DNA version or provirus, migration to the nucleus and integration of the DNA into the target cell genome. The gene products of gag-pol are also involved in the infection process. Transduction is a term used to describe this process for retroviral vectors and for replication competent retroviruses carrying heterologous genetic material in the genome. Generally, transduction is used to refer to the process of introducing a foreign gene, particularly a therapeutically active gene, into a target cell by means of a retroviral vector.

Thus, improved infection of a target cell may be associated with env or with gag-pol, or it may be associated with a part of the viral or vector genome which is not env or gag-pol, or it may be associated with a combination of any or all of these.

In particular for the purpose of gene therapy, there is a need for retroviral vectors which are better able to infect certain cell types than existing vectors. Such cell types include for example human primary blood lymphocytes and cancer cells. When generating virus or vectors better able to infect a chosen cell type, it will be preferable to do so using host cells which are as similar as possible to the chosen cell type. For practical reasons, the host cells will generally be from a cell line, which may be derived from primary cells of the chosen cell type. Alternatively, it may be possible to use a supply of primary cells of the chosen cell type. One possible strategy is to use a two stage selection process, evolving the virus or vector first on a cell line and then on fresh primary cells.

The retroviral vectors resulting from the selection process in the method according to the invention may be immediately useful in applications such as gene therapy. Usually however modifications will first of all be required. Typically, the retrovirus or retroviral vector resulting from the selection process of step (ii) of the method according to the invention is used to provide one or more components of a retroviral vector production system for producing retroviral vectors useful for gene therapy or other medical applications. A retroviral vector production system requires packaging components for packaging a suitable vector genome. Depending on the characteristics selected for, the retrovirus or retroviral vector may be used to contribute to the packaging components or the genome or both.

In one particular embodiment of the method according to the invention a starting retroviral vector comprising the env gene and a genome having a selectable marker is subjected to a selection process designed to achieve more efficient infection of a particular target cell. The env gene from the retroviral vector which emerges after the selection process may then be transferred into a packaging cell line which can then be used to produce retroviral vectors having the selected characteristic and suitable for use in a desired application. The retroviral vectors produced by the packaging cell do not carry the env gene, but comprise envelope proteins encoded by the env gene.

In another embodiment, a starting retrovirus having a selectable marker is used. Following a process of selection during which the retrovirus evolves to become more efficient at infecting a chosen target cell, the env and gag-pol genes of the virus which emerges are transferred into expression vectors for use in a retroviral vector production system.

A retroviral vector production system as referred to herein comprises packaging components, that is a set of nucleic acid sequences which encode the packaging proteins need to package a defective retroviral vector genome. When a nucleic acid sequence encoding a compatible packagable RNA genome is introduced into the system, retroviral vectors may be produced by the system. The packaging components are maintained in cells into which they have been either transiently or stably transfected. Most commonly these are cell lines in which the packaging components are stably maintained.

It is a particular aim of this invention to provide new retroviral vector systems derived from new variants of amphotropic and ecotropic viruses produced by in vitro evolution. These variants are selected for their ability to infect specific target cell types or to have specific properties that are desirable. Selection protocols vary with different desired end-points but several general principles are taken into account.

1. Varying the mutation rate.

One of the most powerful optimisation procedures in physics/computing is "simulated annealing" (Kirkpatrick S et al, Science 220, 671, 1983,Gillespie D T, J Comp Phys 22, 403, 1976). Varying temperature gradients are used to aid the search for the global minimum and avoid the chance of being trapped in a local minimum. For our system, temperature is equivalent to mutation rate. Alternating the mutation rate in serial passages could greatly improve the chances of finding optimal variants. (For a theoretical description see Fontana W et al, Phys Rev A 40, 3301, 1989.) The idea is to use a very high mutation rate in one culture, in order to produce many mutants and subsequently to use a very low mutation rate in the next culture, in order to provide a chance for the best variants to outgrow the others without accumulating too many additional mutations.

2. Optimal mutation rate.

As far as possible the error rate of the MLV reverse transcriptase should be increased to maximise the production of advantageous mutations during the high mutation rate stages. In order that selection works efficiently it is essential to have enough genetic variation. If mutation rates are too low advantageous variants may not appear fast enough and the in-vitro evolution will take too long. On the other hand, for very high mutation rates an advantageous mutation may often be accompanied by a deleterious mutation somewhere else in the genome. In between there is an optimal mutation rate. A very rough estimate shows that the optimal mutation rate is of the order of 1 over the length of the genome (number of bases) (Nowak 1990, Nature 347, 522). For a genome of the size of MLV the optimal mutation rate is approximately $10^{-3}$–$10^{-4}$.

3. Controlling the mutation rate in vitro.

Given the considerations above it is important to be able to vary mutation rate during the evolution protocols so that the system goes through alternating rounds of generation of diversity and selection. Adding high concentrations of nucleosides or sub-inhibitory concentrations of nucleoside analogues to producer cell cultures increases the error rate of reverse transcriptase (e.g. Pathak and Temin 1992 J. Virol. 66, 3093). This technique is used, therefore, to alter the mutation rate during the selection protocols. Mutation rates can be measured by the procedures described by Pathak and Temin (1992) in experiments that are run in parallel with the selection protocols.

4. Restricting selection to a specific part of the life-cycle of the virus.

In some cases it may be important to evolve components of the vector selectively. Essentially we want to find a variant that is well adapted to infect human cells rather than a variant that is capable of higher level production. Thus we want to maximise the rate and efficiency of the first half of the life-cycle, that is infection, including virus entry, unpacking, reverse transcripton, migration to the nucleus, and integration. By straightforward selection for fast replicating strains we do not differentiate between applying selection pressure to improve infection or improve virus production from infected cells. We can adopt, therefore, various strategies to separate infection from production in the evolution protocol.

i. Infection pulse. In this strategy we would allow infection to occur for only a short time by adding a retrovirus inhibitor eg AZT or other reverse transcriptase inhibitor to inhibit further infection. This procedure would select for those viruses that could infect rapidly.

ii. Component specific evolution. In this system each of the three components, gag-pol, env and genome, of the retroviral vector can be evolved separately in a selection protocol that substantially reduces the probability of selecting for increased virus production in the context of the whole virus. For example, if one wishes to select env variants that increase the infection of a particular target cell line a system such as that shown in FIG. 1 may be used. The key component in the system shown in FIG. 1 is the vector genome which contains both the env gene that is to be the subject of the evolution procedure and a selectable marker such as the neo gene. First a virus vector population is generated by transfecting 293T, or other cells, with a plasmid containing the proviral version of this vector genome. The cells contain a gag-pol expression cassette. The vector genome is transiently expressed and packaged into virus vector particles that can be recovered in the cell culture supernatant. This population of particles is then used to start the rounds of diversity generation and selection. Target cells, again expressing a gag-pol cassette, are transduced and transductants are selected on G418. This step is both a diversity generation step and a selection step. Diversity is generated because of the error-prone reverse transcription step necessary for integration and selection for envelope 'efficiency' is achieved because receptor binding and entry is essential for transfer of the neo gene. The $G418^r$ population of transduced cells is then used to produce more virus vector particles and these are used to transduce a fresh batch of target cells for second round of selection. This can go on for many rounds until the efficiency of the transduction is seen to increase. At this stage the envelope component can be separated from the genome and used in a 'conventional' vector production system. The resulting new vector production system has an env gene component that is now optimised for infection/transduction of the target cells. Similar strategies can be used for the genome alone to optimise packaging, for example, and for gag-pol to optimise particle formation, reverse transcription and integration.

5. Time schedule for serial transfer.

It might be essential to keep the virus in exponential growth phase. This means that there should always be enough infectable cells in the culture. In other words sampling should occur early on in the infection selection process.

6. Recombination

Running several lines in parallel (e.g. Schober A et al, BioTechniques 18, 4, 1995) and ocassionally recombining them should greatly enhance the efficacy of the search process for optimally adapted viruses. The theory of genetic algorithms (Holland J H, Adaptation in natural and artificial systems, Ann Arbor: Univ of Michigan Press, 1975) suggests that under specific circumstances recombination leads to better optimization procedures (Kauffman S, The origins of order, OUP, 1993). Recombination may be achieved in vivo by using virus derived from several selection strategies in a single selection scheme or recombination in vitro may be achieved using PCR.

7. Computer models

All diversity/selection systems can be modelled on a computer to give an estimate of rates and probabilities of achieving specific evolutionary endpoints. We refer to this as CATORV (computer aided target optimized retroviral vector). The simulations are based on quasi-species theory (Eigen M, Schuster P, The Hypercycle, Springer, Berlin 1979, Eigen M, McCaskill J, Schuster P, J Phys Chem, 92, 6881, 1988) using concepts like sequence space and fitness landscape.

BRIEF DESCRIPTION OF THE DRAWINGS

The invention is further illustrated in the attached figures in which.

Figure Legends

Figure 1:
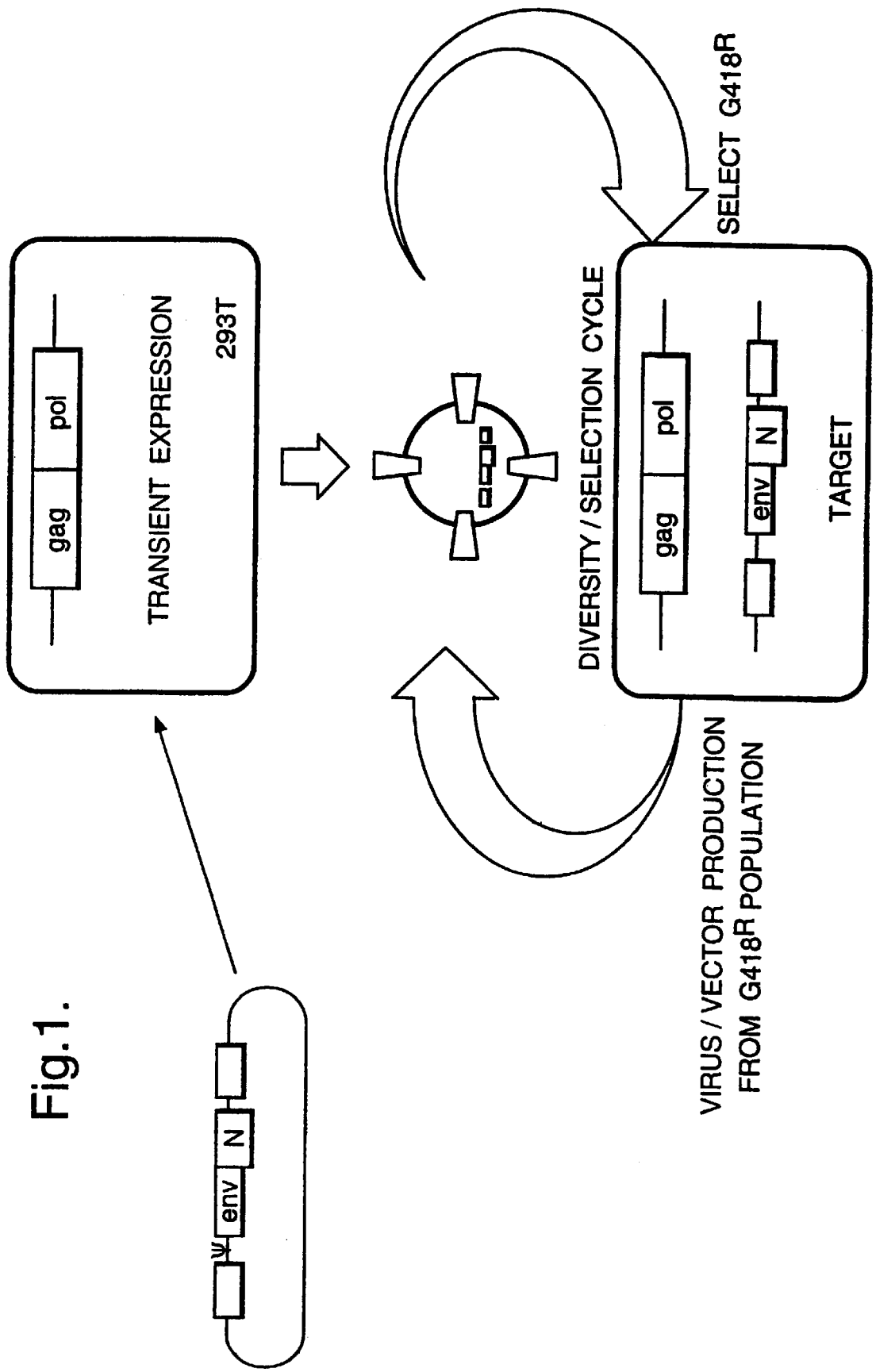
FIG. 1 shows the principle of selective evolution of a retroviral component.

FIG. 1—A plasmid containing a retroviral vector genome containing an env gene and a $neo^r$ gene is transiently expressed in a producer cell such as 293T, containing the necessary packaging components. Retroviral vector particles are produced and are contacted with a chosen host cell for successive rounds of infection. Infected host cells are selected for using $G418^R$.

Figure 2:
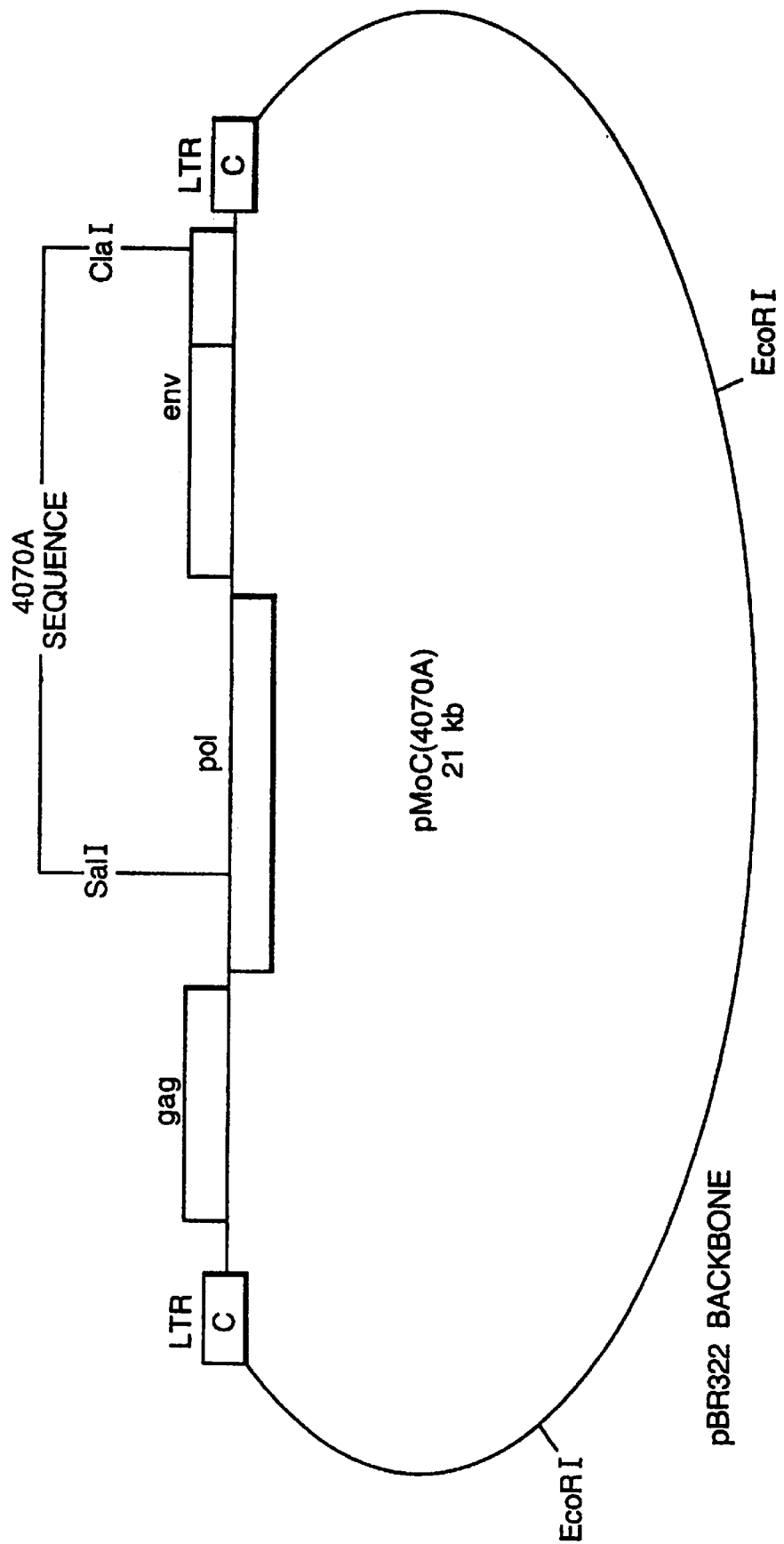
FIG. 2 shows a plasmid designated pMoC(4070A) containing an amphotropic MLV provirus.

FIG. 2—pMoC(4070A) is a derivative of pMo(4070A) (Ott et al 1992) in which the U3 regions of the LTRs contain the CMV-IE enhancer.

Figure 3:
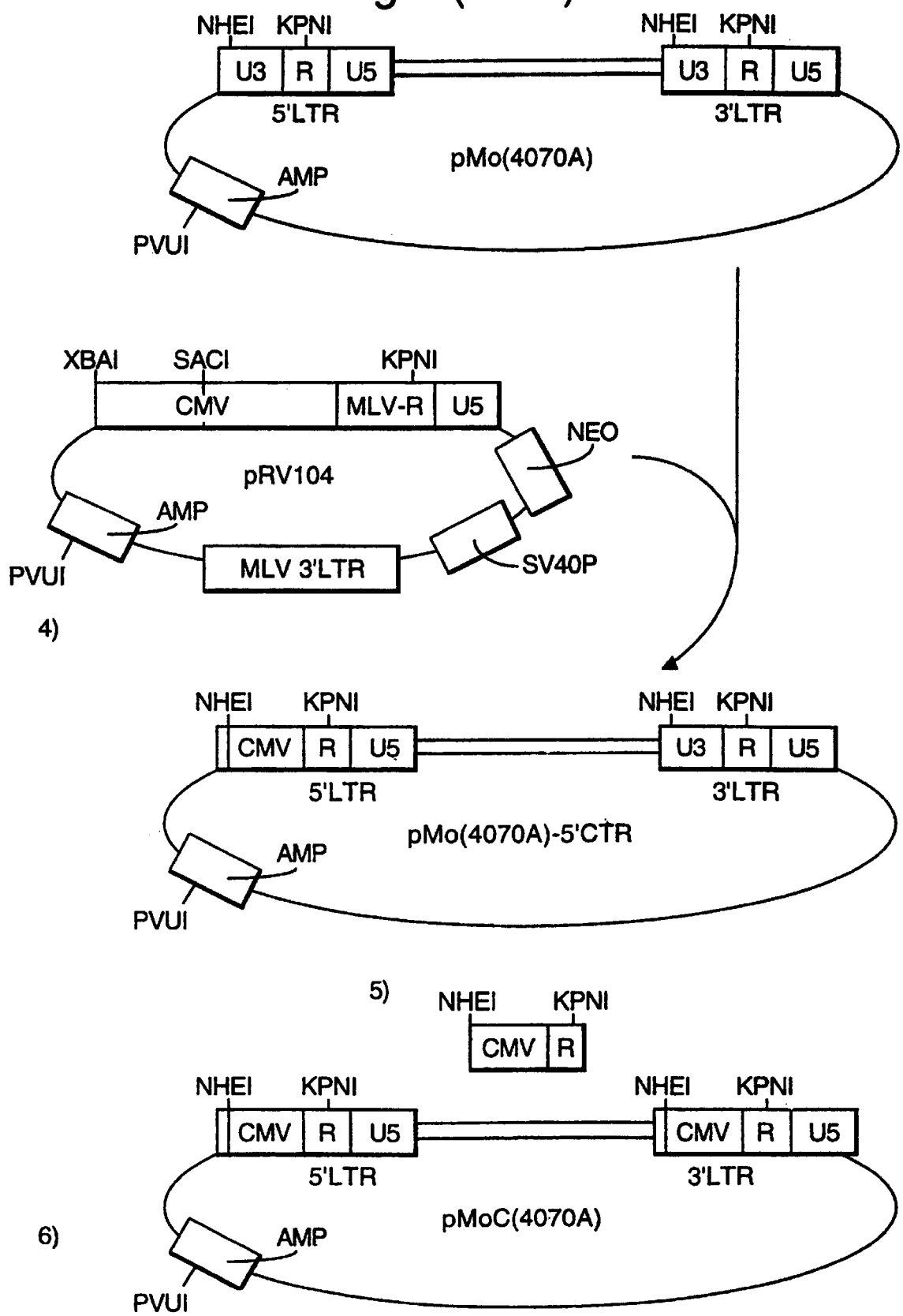
FIG. 3 shows a scheme for the construction of the plasmid shown in FIG. 2.

FIG. 3—Construction of pMoC(4070A) is carried out as follows:

1) Double stranded oligonucleotide was synthesised to span the SAC1 site at −13 in the CMV promoter to the KPN1 site at +36 in the MLV R region such that +1 for the CMV promoter and +1 for the MLV R region coincide (Shinnick et al, 1981, Nature 293, 543). This was inserted into pSP46 (Ogden et al., 1986, MCB 6, 4335)

2) Remaining CMV promoter sequences restored by inserting 530 bp XBAi-SACI fragment from pKV461 (Adams et al., 1988, NAR 16, 4287) into the pSP46 plasmid containing the fragment described in 1)

3) The PVUI-KPNI fragment from above containing the CMV promoter replaces the corresponding sequence of pLNSX (Miller and Rosman, 1989, Biotechniques 7, 980) to create pRV104.

4) Replace PVUI-KPNI fragment in pMo(4070A) with PVUI-KPNI fragment from pRV104.

5) Excise XBAI-ECORI fragment from pRV104 and add NHEI linkers. Cut with KPNI to produce the fragment shown.

6) Insert this fragment into pMo(4070A)-5'CTR cut with NHEi and KPNI. Partial digests are required. This gives the plasmid shown.

Figure 4:
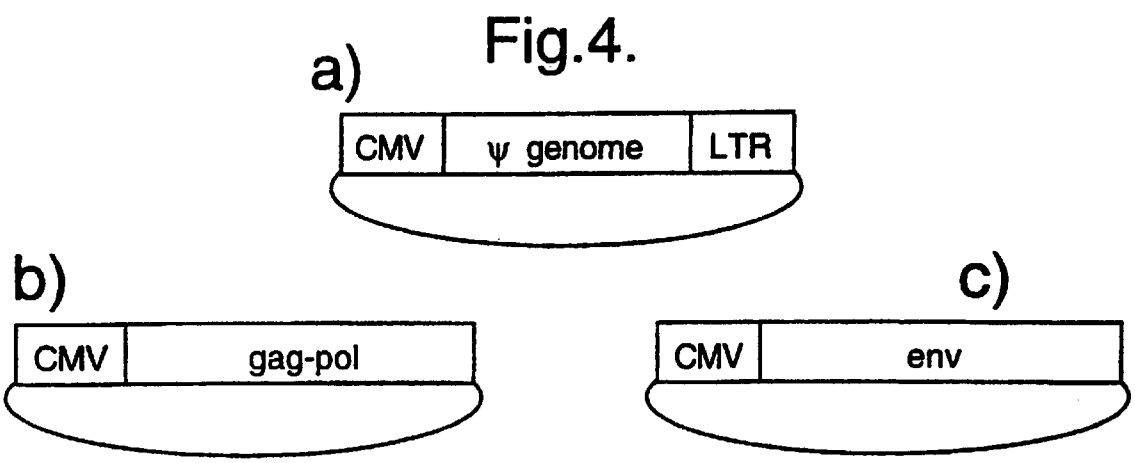
FIG. 4(parts *a–c*) shows retroviral vector plasmids derived from retroviruses selected by evolution in vitro.

FIG. 4—A general scheme showing retroviral vector plasmids which may be derived from retroviruses selected by evolution in vitro. They may be for example a) pHITIII, or derived from a selected genome; b) pRV-VI-51; c) pRV-VI-52, all of which are described in Example 1.

The invention will now be further described in the examples which follow.

EXAMPLES

Example 1

A major goal in gene therapy is the transduction of human primary blood lymphocytes (PBLs) for the treatment of inherited diseases such as SCID, acquired diseases such as leukaemia and infectious diseases such as AIDS. Although, amphotropic vector preparations can be produced readily with titres of $10^6$–$10^7$ on NIH 3T3 or HeLa cells these same preparations transduce PBLs at efficencies 34 orders of magnitude lower. An MLV vector derivative with a high transduction efficiency is needed urgently therefore.

As a first step towards this goal, a replication competent amphotropic MLV provirus is needed. We have used a derivative of a construction designated Mo(4070A) described by Ott et al. (1992). This is a chimeric genome in which the amphotropic envelope gene from virus isolate 4070A (Rasheed et al., 1976) replaces the ecotropic envelope gene in a Mo-MLV backbone. This provirus, together with some genomic flanking sequences is present in a pSV2neo plasmid the whole molecule being designated pMo(4070A). The derivative that we have produced, designated pMoC(4070A) contains the CMV-IE promoter in place of the MLV promoter in the U3 region of both LTRs (FIG. 2). pMoC(4070A) was constructed according to the scheme shown in FIG. 3 although other strategies could be used to produce the same molecule or to produce molecules with other efficient promoters in the U3 regions. This derivative was produced in order to increase the production of genomes in human cells thereby achieving larger populations and therefore greater diversity.

In addition, by ensuring that genome production is not limiting we reduce the probability of selecting variants that simply have a greater capacity for production. Any amphotropic provirus in any plasmid would be equally suitable but it is likely that enhanced expression from the LTRs would be required to generate the population sizes necessary for the evolution strategies.

Plasmid pMoC(4070A) is used to transfect 293T cells to produce a primary virus stock. As an index of the virus concentration in this stock reverse transcriptase (RT) levels are measured and compared with those of a vector preparation of known transducing titre. Levels of reverse transcriptase are typically 100–200 units/ml which corresponds to a transducing titre of about $10^6 10^7$ cfu/ml. This represents the starting master stock to be used for the selection process and as a reference stock against which new variants are compared.

One milliliter of this stock is used to infect $5 \times 10^5$ HeLa cells and $5 \times 10^5$ PBLs. Two hours later the medium is changed and 6 days later RT levels are measured. Typically the levels from virus plated on PBLs is 34 orders of magnitude lower than with HeLa cells. This represents the difference in plating efficiency of the two cell types. The PBLs are maintained for 20 days in order to allow replication and selection to occur and then 5ml supernatant from the PBLs is plated on $5 \times 10^5$ HeLa cells to amplify the population over a period of a few days until the supernatant RT levels are equivalent to a particle titre of about $10^6$/ml. 2 ml of this HeLa supernatant is plated on $5 \times 10^5$ PBLs and the PBLs are maintained for 20 days to allow further selection to occur. During both the amplification stage on HeLa cells and the selection on PBLs the infection is monitored every 4 days by immunofluorescence using anti-env antibody and RT to detect any emerging virus. This cycle of PBL-Hela-PBL is designated one round of selection.

After several rounds of selection 1 ml of the virus supernatant is plated on PBLs and HeLa and 2 hours later the medium is changed and 6 days afterwards RT levels are measured. A reduction of the difference between the two cell types shows that an MLV variant is emerging with increased infectivity for PBLs. This strategy is employed in 10 parallel tracks of selection in order to produce 10 different selected populations. These new populations presumably comprising variants with increased replication capability on PBLs are designated $MLVP^{PBL1-10}$. These are then combined and several rounds of selection are carried out with the mixed virus populations at high multiplicities of infection in order to facilitate recombination and competition. At the end a virus maximally adapted to growth on PBLs emerges. This virus is designated $MLV^{PBL-V1}$.

$MLV^{PBL-V1}$ is then used to produce plasmids for helper-free vector production following standard procedures described in papers such as Soneoka et al. (1995) and Miller and Rossman (1989) and references therein. These have the characteristics of the plasmids shown in FIG. 4. These are designated pRV-V1-51 (gag-pol) and pRV-V1-52 (env). These two plasmids are then used to transduce 293T cells with pHIT111 (a lacZ carrying vector genome plasmid) (Soneoka et al., 1995) to produce a vector stock which is titred on NIH 3T3 cells and HeLa cells and then used to transduce PBLs. The PBLs are then stained for expression of B-galactosidase. A similar experiment is carried out with a standard amphotropic vector system and the numbers of blue cells compared. The vector produced from the $MLV^{PBL-V1}$ components gives substantially greater numbers of blue PBLs demonstrating that the new vector system has increased transducing potential for PBLs. This vector system will be of greater use therefore in gene therapy protocols requiring gene transfer into PBLs.

We have called these new vectors Target Optimised Retroviral Vectors (TORVs)

Example 2
MLV Variant Adapted for Infection of Human Ovarian Cancer Cells (SW626)

The producer cell line 293T was transiently transfected with 5 µg of pMoC(4070A) using the overnight calcium phosphate method described by Gorman et al. (1985). Viral supernatant was harvested 48 hours post-transfection and filtered using a 0.45µm filter (Sartorius). MLV RT levels (Goff et al. 1981) were converted to the viral titre from a standard curve relating RT activity to viral titre.

Figure 5:
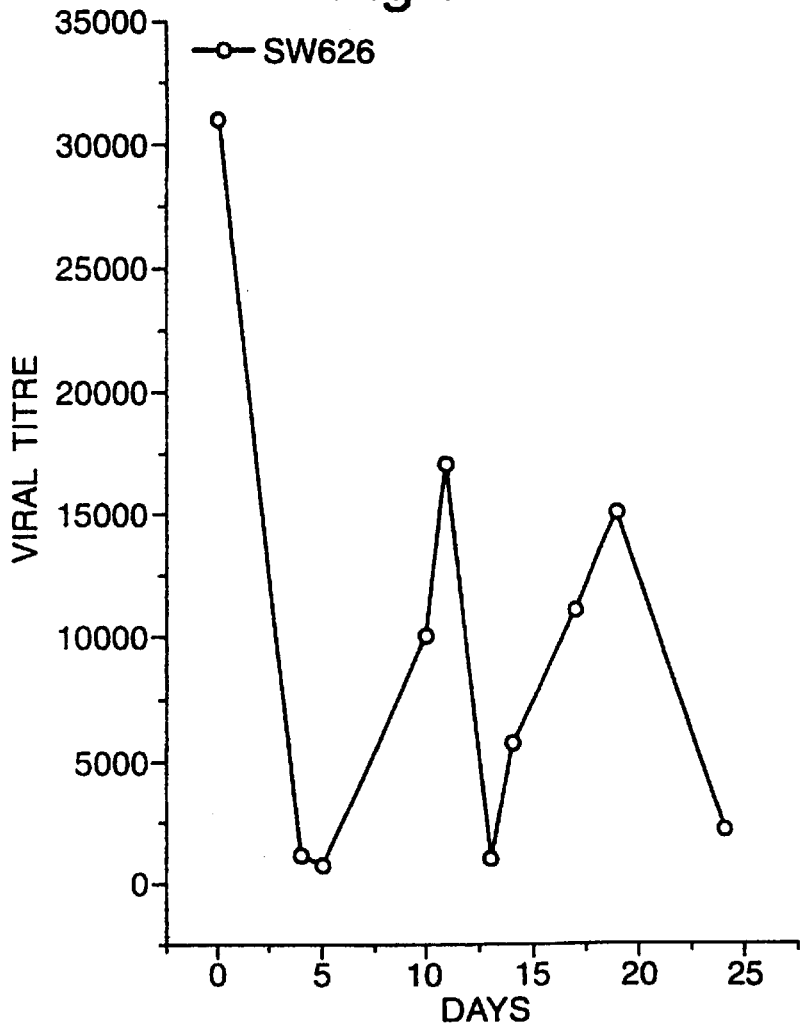
FIGS. 5 to 7 show viral titres obtained in the viral evolution method described in Example 2.

The target cancer cell line SW626 was plated at a density of $1.0 \times 10^6$ cells in a 75 cm flask and infected with 3 mls of filtered viral supernatant in a total of 5 mls of complete medium containing 8 µg/ml of polybrene. Twelve hours later fresh medium was added to the infected cells. Once the cells had reached 90% confluency the cells were split 1:5. Samples of virus supernatant were collected routinely throughout the experiment and stored at −70° C. The growth pattern of the virus MOLV4040A in SW626 cells was followed over a 25 day period. The infected cells were split 5 times during this time period on days 3, 5, 11, 16 and 22 and triplicate viral supernatant samples were taken on days 3, 5, 8, 9, 11, 12, 15, 16, 17, 22 and 25. It should be noted that no new (uninfected) cells were added to the system during this time period. Cells were monitored continuously for phenotypic changes to determine whether the virus had a detrimental effect on them. The viral growth pattern of MOLV4070A in SW626 cells was analysed by MLV RT assays and viral titres were determined (FIG. 5) as described before. Virus production in SW626 cells produced titres up to $1.5 \times 10^4$ on days 10 and 20. The peaks and troughs of viral titre observed from the infected SW626 cells reflects the splitting of these. However it was clear from these data that a chronically infected cell line had been established. A sample of virus was stored at this time and designated MLV626-0.

Virus from SW626 cells chronically infected with MOLV4070A was used to infect new uninfected cells which were plated out at a density of $2 \times 10^6$ in a 75 cm flask. Triplicate viral supernatant samples were taken every 2 to 3 days. Once the cells had reached 90% confluency the virus supernatant was harvested, filtered (0.45 µm filter, Sartorius) and used to infect new uninfected SW626 cells plated at the same density as before. Samples of virus supernatant were collected routinely and stored at −70° C. MLV RT assays and hence viral titres were determined every 14 days in order assess the growth pattern of the virus. This pattern of infecting new SW626 cells was maintained continuously until there was evidence of a new MOLV4070A variant (FIG. 6).

Figure 7:
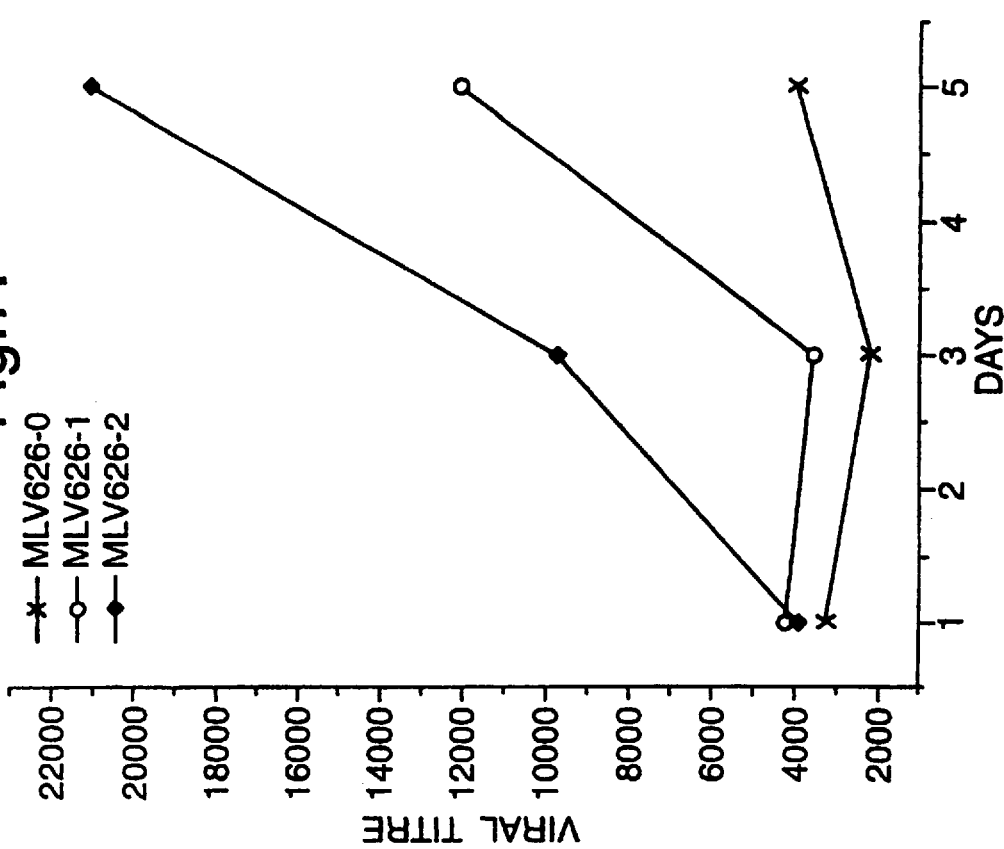
Figure 6:
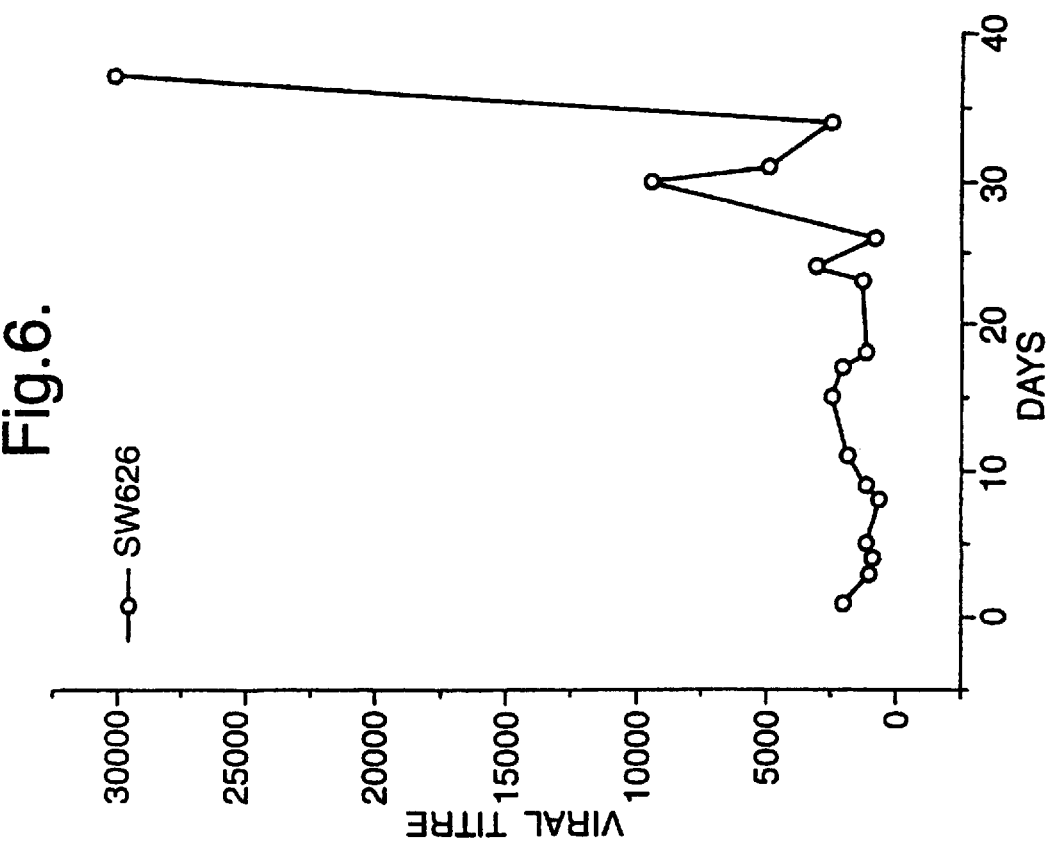

In FIG. 6 it appeared that by day 34 a new MOLV4070A variant population had emerged, this variant was designated MLV626-1. The new variant population was grown for a further 41 days using the same passaging protocol. The resulting population was designated MLV626-2. Populations MLV626-0, MLV626-1 and MLV626-2 were then compared by infecting new uninfected SW626 cells and monitoring growth patterns over a 5 day period. MLV RT assays were performed and the viral titres calculated. The results are shown in FIG. 7. It appears that the new variant MLV626-1 infected SW626 cells more efficiently than the starter virus MLV626-0 with viral titres of $1.2 \times 10^4$ for MLV626-1 and $3.9 \times 10^3$ for MLV626-0 on day 5. Interestingly, however, the virus MLV626-2 had a viral titre of $2.4 \times 10^4$ which was higher than the titre of MLV626-1. It appears that MLV626-1 and MLV626-2 are in fact new variants of MOLV4070A and that these variants have the ability to infect SW626 cells more efficiently than the starter virus MLV626-0.

SW626 cells infected with either MLV626-1 or MLV626-2 were diluted so that 10 cell populations were isolated in a well of a forty-eight well plate and allowed to grow to 80%–85% confluence. A MLV RT assay was performed on virus supernatant from each isolated SW626 cellular population. Products of the reaction were spotted onto DE81 paper and examined by autoradiography. The MLV626-2 clones producing the strongest signals were selected. These clones were then expanded and total DNA prepared according to the method of Blin and Stafford (Nucl. Acids. Res 3, 2303.1976). This DNA was then used as a template for two PCR reactions. The first reaction, carried out using Advantage PCR kit (Clontech), used a 5' primer CGCGGATCCGMTTCATGGGCCAGACTGT-TACCACTCCC [SEQ ID NO: 1] and a 3' primer CGCGTC-GACTCTAGATTAGGGGGCCTCGCGGGTTTMCCTTA [SEQ ID NO: 2] and produced a fragment of 5.2kb comprising the gag-pol cassette. The second reaction, again using the Advantage PCR kit, used a 5' primer CGCGCTAGCTCTAGMTGGCGCGT-TCAACGCTCTCAAAA [SEQ ID NO: 3] and a 3' primer CGCGGATCCTCATGGCTCGTACTCTATGGGTTT [SEQ ID NO: 4] and produced a 2 kb fragment comprising the amphotropic env cassette. The 5.2 kb fragment was cut with EcoRi and Sall and inserted into pCIneo (Promega) to produce a gag-pol expression plasmid designated pE6262 and the 2 kb fragment was cut with Nhel and EcoRi and also inserted into pCIneo to produce and env expression plasmid designated pGP6262.

Plasmids pE6262 and pGP6262 were then used as the gag-pol and env expression plasmids in a 3-plasmid transfection system to produce lacZ transducing retroviral particles (Soneoka et al).

Example 3

Many metabolic deficiencies are the result of low or absent levels of proteins in the liver. Efficient gene transfer to the liver is an important aspect, therefore, of future gene therapy strategies. Using similar strategies to those used in Examples 1 and 2 we produce a TORV for hepatocytes. This will increase the ability to deliver genes to the liver.

Example 4

Murine retroviruses are known to be inactivated by complement components present in human serum (Takeuchi et al., 1994).

This seriously limits the ability to use MLV-based retrovirus vectors in vivo. This is known to be partially alleviated by preparation of the vector particles in non-murine cells (James Respess, pers. comm.; Takeuchi et al., 1994) although the particles are still somewhat sensitive. Using similar strategies to those used in Examples 1 and 2 we produce a retroviral vector system that has increased resistance to inactivation by human complement. Instead of using target cell types for the selection stage we use exposure to human serum. In particular high titre retrovirus preparations produced in either murine 3T3 cells or HeLa cells or any other cells type are exposed to different concentrations of human serum. Concentrations are from neat to a 1/1000 dilution in buffer (Takeuchi et al., 1994). After 2 hours exposure, and therefore selection, remaining virus is plated onto fresh cells in order to allow amplification of the selected population. This represents one round of selection. Many rounds of selection are carried out until the maximum resistance to exposure to human serum is achieved. As with Example 1 several parallel variant populations will be selected and then combined in order to allow for recombination. Highly resistant MLV variants will then be used to produce new vector systems as described in Examples 1 and 2. The resulting vector system has greater utility for human gene therapy particularly for those protocols that require delivery in vivo.

Example 5

In many gene therapy situations high titre transducing virus stocks are required. In order to achieve these high titres it is necessary to concentrate the preparation. However, retroviruses are susceptible to the shear forces that occur in most centrifugation or filtration methods (see Burns et al., 1993)). This means that while virus particles are concentrated many of the particles lose their envelope glycoproteins and so the effective transducing titre is reduced. Using similar strategies to those used in Examples 1 and 2 we produce a retroviral vector system that has increased resistance to inactivation by shear forces. In this example selection is imposed on the population by exposing the virus to the shear forces inherent in passing through a gauge 10 syringe needle. Instead of using target cell types for the selection stage we use passage through the syringe needle. In particular, high titre retrovirus preparations produced in either murine 3T3 cells or HeLa cells or any other cell type are passed through a gauge 10 syringe needle from a 5ml. syringe. The remaining virus is plated onto fresh cells in order to allow amplification of the selected population. This represents one round of selection. Many rounds of selection are carried out until the maximum resistance to shearing is achieved. As with Example 1 several parallel variant populations will be selected and then combined in order to allow for recombination. Highly resistant MLV variants will then be used to produce new vector systems as described in Examples 1 and 2. The resulting vector system has greater utility for human gene therapy because higher titres can be achieved by concentration by centrifugation or filtration.

Example 6

A long standing goal of retroviral vector design has been the development of targeted vectors that are able to transduce specific cell types. The advantages of targeted vectors are that vector particles are not 'wasted' on non-target cells and it may be possible to increase the efficiency of gene transfer following administration of the vectors in vivo. A common strategy that has been employed by several laboratories has been the use of vectors bearing manipulated surface proteins. These proteins are generally hybrid molecules comprising the retroviral surface protein backbone with a sequence of amino acids inserted that binds to a specific cell surface molecule on the target cell. Several targeting systems have been produced and these include EPO (Kasahara et al. 1995), single chain antibodies (Somia et al. 1995; Chu and Dornberg 1995), growth factor-like sequences (Han et al. 1995; Cosset et al. 1995) and integrin-binding peptides (Valsesia-Wittman et al. 1994). In some of these cases transduction of the specific target cell is achieved. However, in many of these cases efficiencies are low and there is a need for the inclusion of the wild-type surface protein in the targeted particles. This makes them of very limited use in therapeutic applications.

It is possible to increase the efficiency of these manipulated is targeted systems by applying the principles described in the previous examples. If the manipulated surface protein gene is incorporated into a replication competent provirus then increased efficiency can be selected by passaging the virus on the target cells. Alternatively, a manipulated surface protein gene can be incorporated into a retroviral vector genome and increased efficiency selected by component specific evolution (FIG. 1).

Using these strategies, for example, in the system described by Han et al. (1995) it is possible to substantially increase the efficiency of gene delivery to breast cancer cells by retroviral vector particles bearing a hybrid surface protein containing heregulin. Replication competent retroviruses in which the natural surface protein gene is replaced by the heregulin hybrid are passaged on MDA-MB453 or other breast cancer cell lines. These cell lines could include the gene for wild-type ecotropic envelope proteins in the early stages of selection in order to facilitate infection of the target cells. Later in the selection scheme it may be possible to use unmanipulated cells if the selection process had yielded virus that no longer requires the wild-type surface protein to infect the target cells. When vector systems are produced from these selected viruses they transduce breast cancer cells at efficiencies that make them clinically useful for the treating of breast cancer by gene therapy.

REFERENCES

Albritton, L. M., Tseng, L., Scadden, D., & Cunningham, J. M. (1989) Cell 57, 659–666.

Battini, J -L., Heard, J. M., & Danos, O. (1992) J. Virol 66,1468–1475.

Burns, J., Friedmann, T., Driever, W., Burrascano, M., Yee, J -K. (1993) Proc. Natl. Acad. Sci. USA 90:8033–37.

Chu and Dornberg (1995) J. Virol. 69,2659.

Cone, R. D. & Mulligan, R. C. (1984) Proc. Natl. Acad. Sci. USA 81: 6349–53.

Cosset et al. (1995) J. Virol. 69, 6314.

Goff et al. (1981) J. Virol. 38, 239

Gorman et al. (1986) DNA Cloning Virol. A Practical Approach. IRL Press

Grossman, M., Raper, S. E., Kozarsky, K., Stein, E. A., Engelhardt, J. F., Muller, D., Lupien, P. J. & Wilson, J. M. (1994) Nature Genetics 6, 335–41.

Han et al (1995) Proc. Natl. Acad. Sci. USA 92,9747.

Hartley, J. W. & Rowe, W. P. (1976) J. Virol. 19:19–25.

Hunter, E. & Swanstrom, R. (1990). Curr. Top. Microbiol. and Immunol. 157: 187–253.

Kasahara et al (1995) Science 266, 1373.

McClaughlin, J. R., Cornetta, K., Eglitist, M. A., & Anderson, W. F. (1990) Prog. Nucl. Acids Mol. Biol. 38: 91–135.

Miller, D. G., Edwards, R. H., & Miller, D. (1994) Proc. Natl. Acad. Sci. U.S.A. 91, 78–82.

Moen, R., Karson, E. M., Lotze, M. T., Yang, J. C., Topalian, S. L., Merino, M. J., Culver, K., Miller, A. D., Blaese, R. M., & Anderson, W. F. (1990). N. Eng. J. Med. 323, 570–78.

Morgan, R. A. & Anderson, R. F. (1993) Annu. Rev. Biochem. 62, 192–217.

Oft, D. E., Keller, J., Sill, K. & Rein, A. (1992) J. Virol. 66 6107–116.

Rasheed, S., Gardner, M. B., Chan, E. (1976) J. Virol. 19: 13–18.

Rosenberg, S. A., Aebersold, P., Cornetta, K., Kasid, A., Morgan, R. A.,

Sanes et al. (1986) EMBO. J 5, 3133.

Somia et al (1995) Proc. Natl. Acad. Sci. USA 92, 7570.

Soneoka, Y. Cannon, P. M., Ramsdale, E. E., Griffiths, J. C., Romano, G., Kingsman, S. M. & Kingsman, A. J. (1995) Nucl. Acids Res. 23 628–33.

Takeuchi, Y., Cosset, F -L. C., Lachmann, P. J., Okada, H., Weiss, R. A., Collins, M. K. L. (1994) J. Virol. 68: 8001–8007.

Valsesia-Wittman et al (1994) J. Virol. 68,4609.

Van Zeijl, M., Johann, S. V., Closs, E., Cunningham, J., Eddy, R., Shows, T. B. & O'Hara, B. (1994) Proc. Natl. Acad. Sci., 91,1168–1172 (1994).

What is claimed is:

1. A method of making a retroviral vector having one or more of the following selected characteristics: an increased ability to infect a chosen target cell, or increased resistance to shear forces or increased resistance to human serum, which method comprises:
   (i) providing a starting retrovirus or retroviral vector, and a host cell for the retrovirus or the retroviral vector;
   (ii) subjecting the starting retrovirus or retroviral vector to a selection process in vitro which selection process involves a plurality of rounds of infection of the host cell during which the retrovirus or retroviral vector evolves to attain the selected characteristics; and
   (iii) where a starting retrovirus is provided in (i), the retrovirus resulting from (ii) is used in at least one component of a retroviral vector production system for producing retroviral vectors having the selected characteristic or characteristics.

2. A method as claimed in claim 1, wherein the host cell is a chosen target cell and the selected characteristic is an increased ability to infect the target cell.

3. A method as claimed in claim 1, wherein the selection process involves exposing the retrovirus or retroviral vector to shear forces or human serum between rounds of infection, and the selected characteristic is an increased resistance to shear forces or an increased resistance to human serum, respectively.

4. A method as claimed in claim 1, wherein the selected characteristic is a property or a packaging component or components of the retrovirus or the retroviral vector.

5. A method as claimed in claim 1, wherein the retrovirus or retroviral vector is, or is derived from, MLV.

6. A method as claimed in claim 1, for making a retroviral vector for use in gene therapy.

7. A method as claimed in claim 1, wherein the starting retrovirus or retroviral vector comprises a selectable marker.

8. An evolved retroviral vector made by the method according to claim 1, wherein the retroviral vector has an increased ability to infect a chosen target cell and/or increased resistance to shear forces.

9. An evolved retroviral vector production system, said system having at least one component having a selected characteristic or characteristics attained by the method according to claim 1 and transferred from the retrovirus or retroviral vector into the retroviral vector production system said component conferring upon the retroviral vector an increased ability to infect a chosen target cell and/or increased resistance to shear forces.

10. An expression vector comprising a packaging component having a selected characteristic of a retrovirus or a retroviral vector obtained by the selection process (ii) of the method according to claim 1 and having an increased ability to infect a chosen target cell and/or increased resistance to shear forces.

11. An expression vector encoding a genome of a retroviral vector, which genome is derived from the genome of a retrovirus or retroviral vector resulting from the selection process (ii) of the method according to claim 1 and having an increased ability to infect a chosen target cell and/or increased resistance to shear forces.

12. A method as claimed in claim 2, wherein the starting retrovirus or retroviral vector comprises a manipulated surface protein gene and the selected characteristic is an increased ability to infect the target cell via the surface protein encoded by the manipulated surface protein gene.

13. A method as claimed in claim 2, wherein human lymphocytes or hepatocytes or cancer cells are the chosen target cell.

14. A method as claimed in claim 4, wherein a starting retroviral vector is used which comprises a selectable marker and the packaging component or components.

15. A method as claimed in claim 4, wherein the packaging component is env.

16. A method as claimed in claim 4, wherein the packaging components are env and gag-pol.

17. A method as claimed in claim 14, wherein the packaging component or components of the retroviral vector resulting from the selection process (ii) is or are used in a retroviral vector production system to produce retroviral vectors having the selected characteristics.

18. An evolved retroviral vector as claimed in claim 8, having a genome containing a therapeutically active gene.

19. An evolved retroviral vector production system as claimed in claim 9, comprising a packaging cell line transfected with a DNA construct encoding a packagable retroviral vector genome.

20. A packaging cell line of a system according to claim 19, having a selected characteristic associated with it.

* * * * *

UNITED STATES PATENT AND TRADEMARK OFFICE
CERTIFICATE OF CORRECTION

PATENT NO. : 6,168,916 B1
DATED : January 2, 2001
INVENTOR(S) : Kingsman et al

It is certified that error appears in the above-identified patent and that said Letters Patent is hereby corrected as shown below:

Column 8,
Line 10, "$10^6 10^7$" should read -- $10^6$-$10^7$ --

Column 10,
Line 18, "M" should read -- AA --

Column 14,
Line 49, "or" should read -- of --

Signed and Sealed this

Eleventh Day of June, 2002

*Attest:*

JAMES E. ROGAN
*Attesting Officer*   *Director of the United States Patent and Trademark Office*